(12) United States Patent
Hoeppner (10) Patent No.: US 9,211,487 B2
(45) Date of Patent: Dec. 15, 2015

(54) STERILE BLOOD SEPARATING SYSTEM (71) Applicant: Biomet Biologics, LLC, Warsaw, IN (US)

(72) Inventor: Jacy C. Hoeppner, Warsaw, IN (US)

(73) Assignee: Biomet Biologics, LLC, Warsaw, IN (US)

( * ) Notice: Subject to any disclaimer, the term of this patent is extended or adjusted under 35 U.S.C. 154(b) by 323 days.

(21) Appl. No.: 13/975,961

(22) Filed: Aug. 26, 2013

(65) Prior Publication Data

US 2013/0345038 A1   Dec. 26, 2013

Related U.S. Application Data

(62) Division of application No. 12/062,801, filed on Apr. 4, 2008, now Pat. No. 8,518,272.

(51) Int. Cl.
| | |
|---|---|
| *B01D 21/26* | (2006.01) |
| *A61M 1/36* | (2006.01) |
| *B01L 3/00* | (2006.01) |
| *B04B 5/04* | (2006.01) |
| *B04B 7/08* | (2006.01) |
| *B04B 7/02* | (2006.01) |

(52) U.S. Cl.
CPC ......... *B01D 21/262* (2013.01); *A61M 1/3693* (2013.01); *B01L 3/50215* (2013.01); *B04B 5/0442* (2013.01); *B04B 7/08* (2013.01); *B01D 2221/10* (2013.01); *B01L 2200/026* (2013.01); *B04B 2007/025* (2013.01)

(58) Field of Classification Search
USPC ............. 210/513, 121, 787, 782, 109, 512.1, 210/512.3, 518; 494/37, 35, 43, 83
See application file for complete search history.

(56) References Cited

U.S. PATENT DOCUMENTS

| | | | |
|---|---|---|---|
| 1,378,806 | A | 5/1921 | Ausubel |
| 1,948,388 | A | 2/1934 | Liberson |
| 1,950,137 | A | 3/1934 | Dowe |
| 2,112,160 | A | 3/1938 | Johnson |

(Continued)

FOREIGN PATENT DOCUMENTS

| | | |
|---|---|---|
| CA | 2244697 | 8/1997 |
| CA | 2295733 A1 | 1/1999 |

(Continued)

OTHER PUBLICATIONS

G.E. Bollin, J.F. Plouffe, M.F. Para and B. Hackman. Aerosols containing Legionella pneumophila generated by shower heads and hot-water faucets. Appl. Environ. Microbiol. 1985, 50(5):1128. pp. 1128-1131.

(Continued)

*Primary Examiner* — Dirk Bass
(74) *Attorney, Agent, or Firm* — Schwegman Lundberg & Woessner, P.A.

(57) ABSTRACT

A system for separating components of a composition according to density. The system includes a torque generating device, a separation device, and a housing. The separation device separates the composition into different components according to density. The housing accommodates the separation device. The housing includes a base having an interface that transfers torque from the torque generating device to the separation device, a cover, and a conduit for introducing the composition into the separation device without opening the cover.

15 Claims, 3 Drawing Sheets

(56) References Cited

U.S. PATENT DOCUMENTS

| | | |
|---|---|---|
| 2,322,753 A | 6/1943 | Thomas |
| 2,533,004 A | 12/1950 | Ferry et al. |
| 2,915,063 A | 12/1959 | Cutter |
| RE25,113 E | 1/1962 | Wilburn |
| 3,112,747 A | 12/1963 | Cowley |
| 3,215,141 A | 11/1965 | Podhora |
| 3,223,083 A | 12/1965 | Cobey |
| 3,236,418 A | 2/1966 | Dalle et al. |
| 3,314,427 A | 4/1967 | Stafford |
| 3,406,686 A | 10/1968 | Keller |
| 3,435,944 A | 4/1969 | Ishii |
| 3,467,096 A | 9/1969 | Horn |
| 3,473,646 A | 10/1969 | Burke |
| 3,552,394 A | 1/1971 | Horn |
| 3,586,064 A | 6/1971 | Brown et al. |
| 3,625,353 A | 12/1971 | Ishii |
| 3,654,925 A | 4/1972 | Holderith |
| 3,685,248 A | 8/1972 | Godelaine |
| 3,767,085 A | 10/1973 | Cannon et al. |
| 3,780,935 A | 12/1973 | Lukacs et al. |
| 3,800,947 A | 4/1974 | Smith |
| 3,813,072 A | 5/1974 | Moore |
| 3,828,980 A | 8/1974 | Creighton et al. |
| 3,894,952 A | 7/1975 | Ayres |
| 3,901,402 A | 8/1975 | Ayres |
| 3,937,219 A | 2/1976 | Karakashian |
| 3,976,073 A | 8/1976 | Quick et al. |
| 4,021,352 A | 5/1977 | Sarstedt et al. |
| 4,040,420 A | 8/1977 | Speer |
| 4,046,699 A | 9/1977 | Zine, Jr. |
| 4,057,499 A | 11/1977 | Buono |
| 4,121,739 A | 10/1978 | Devaney et al. |
| 4,142,668 A | 3/1979 | Lee |
| 4,184,593 A | 1/1980 | Dorr et al. |
| 4,202,769 A | 5/1980 | Greenspan |
| 4,226,235 A | 10/1980 | Sarnoff et al. |
| 4,260,077 A | 4/1981 | Schroeder |
| 4,269,174 A | 5/1981 | Adair |
| 4,322,298 A | 3/1982 | Persidsky |
| 4,355,739 A | 10/1982 | Vierkotter |
| 4,359,049 A | 11/1982 | Redl et al. |
| 4,375,272 A | 3/1983 | Sutton, III |
| 4,413,773 A | 11/1983 | Rohde et al. |
| 4,424,132 A | 1/1984 | Iriguchi |
| 4,434,820 A | 3/1984 | Glass |
| 4,465,476 A | 8/1984 | Gahwiler et al. |
| 4,467,588 A | 8/1984 | Carveth |
| 4,498,904 A | 2/1985 | Turner et al. |
| 4,524,770 A | 6/1985 | Orandi |
| 4,534,511 A | 8/1985 | Sullivan |
| 4,540,406 A | 9/1985 | Miles |
| 4,610,666 A | 9/1986 | Pizzino |
| 4,627,879 A | 12/1986 | Rose et al. |
| 4,628,969 A | 12/1986 | Jurgens, Jr. et al. |
| 4,631,055 A | 12/1986 | Redl et al. |
| 4,645,073 A | 2/1987 | Homan |
| 4,650,468 A | 3/1987 | Jennings, Jr. |
| 4,673,395 A | 6/1987 | Phillips |
| 4,714,457 A | 12/1987 | Alterbaum |
| 4,734,261 A | 3/1988 | Koizumi et al. |
| 4,735,616 A | 4/1988 | Eibl et al. |
| 4,744,955 A | 5/1988 | Shapiro |
| 4,767,026 A | 8/1988 | Keller et al. |
| 4,818,386 A | 4/1989 | Burns |
| 4,822,340 A | 4/1989 | Kamstra |
| 4,826,048 A | 5/1989 | Skorka et al. |
| 4,828,716 A | 5/1989 | McEwen et al. |
| 4,846,800 A | 7/1989 | Ouriel et al. |
| 4,874,368 A | 10/1989 | Miller et al. |
| 4,877,520 A | 10/1989 | Burns |
| 4,878,903 A | 11/1989 | Mueller |
| 4,902,281 A | 2/1990 | Avoy |
| 4,907,019 A | 3/1990 | Stephens |
| 4,932,942 A | 6/1990 | Maslanka |
| 4,956,883 A | 9/1990 | Lane |
| 4,957,637 A | 9/1990 | Cornell |
| 4,978,336 A | 12/1990 | Capozzi et al. |
| 4,979,942 A | 12/1990 | Wolf et al. |
| 5,009,342 A | 4/1991 | Lawrence et al. |
| 5,032,117 A | 7/1991 | Motta |
| 5,033,252 A | 7/1991 | Carter |
| 5,049,135 A | 9/1991 | Davis |
| 5,074,844 A | 12/1991 | Zdeb et al. |
| 5,080,262 A | 1/1992 | Herold et al. |
| 5,080,283 A | 1/1992 | Kukest et al. |
| 5,104,375 A | 4/1992 | Wolf et al. |
| 5,104,387 A | 4/1992 | Pokorney et al. |
| 5,116,315 A | 5/1992 | Capozzi et al. |
| 5,147,323 A | 9/1992 | Haber et al. |
| 5,152,905 A | 10/1992 | Pall et al. |
| 5,160,021 A | 11/1992 | Sibley et al. |
| 5,176,658 A | 1/1993 | Ranford |
| 5,217,118 A | 6/1993 | Mochizuki et al. |
| 5,219,328 A | 6/1993 | Morse et al. |
| 5,226,558 A | 7/1993 | Whitney et al. |
| 5,226,877 A | 7/1993 | Epstein |
| 5,226,887 A | 7/1993 | Farr et al. |
| 5,253,785 A | 10/1993 | Haber et al. |
| 5,286,257 A | 2/1994 | Fischer |
| 5,290,259 A | 3/1994 | Fischer |
| 5,292,318 A | 3/1994 | Haber et al. |
| 5,298,024 A | 3/1994 | Richmond |
| 5,300,041 A | 4/1994 | Haber et al. |
| 5,308,041 A | 5/1994 | Griffioen et al. |
| 5,314,412 A | 5/1994 | Rex |
| 5,318,524 A | 6/1994 | Morse et al. |
| 5,322,510 A | 6/1994 | Lindner et al. |
| 5,332,092 A | 7/1994 | Fischer |
| 5,354,483 A | 10/1994 | Furse |
| 5,361,906 A | 11/1994 | Sterett |
| 5,368,563 A | 11/1994 | Lonneman et al. |
| 5,372,586 A | 12/1994 | Haber et al. |
| 5,376,079 A | 12/1994 | Holm |
| 5,390,792 A | 2/1995 | Van Ness et al. |
| 5,393,497 A | 2/1995 | Haber et al. |
| 5,393,674 A | 2/1995 | Levine et al. |
| 5,405,607 A | 4/1995 | Epstein |
| 5,409,465 A | 4/1995 | Boggs et al. |
| 5,411,465 A | 5/1995 | Glen et al. |
| 5,419,491 A | 5/1995 | Breitsprecher |
| 5,420,250 A | 5/1995 | Lontz |
| 5,445,614 A | 8/1995 | Haber et al. |
| 5,454,793 A | 10/1995 | Levander et al. |
| 5,458,593 A | 10/1995 | Macabasco et al. |
| 5,464,396 A | 11/1995 | Barta et al. |
| 5,474,540 A | 12/1995 | Miller et al. |
| 5,478,323 A | 12/1995 | Westwood et al. |
| 5,480,068 A | 1/1996 | Frazier et al. |
| 5,480,378 A | 1/1996 | Weis-Fogh et al. |
| 5,484,431 A | 1/1996 | Scharf et al. |
| 5,505,704 A | 4/1996 | Pawelka et al. |
| 5,510,102 A | 4/1996 | Cochrum |
| 5,519,422 A | 5/1996 | Thoman et al. |
| 5,519,931 A | 5/1996 | Reich |
| 5,520,657 A | 5/1996 | Sellers et al. |
| 5,520,658 A | 5/1996 | Holm |
| 5,522,804 A | 6/1996 | Lynn |
| 5,530,531 A | 6/1996 | Girard |
| 5,542,934 A | 8/1996 | Silver |
| 5,549,246 A | 8/1996 | Kukesh |
| 5,549,651 A | 8/1996 | Lynn |
| 5,562,250 A | 10/1996 | O'Neill |
| 5,582,596 A | 12/1996 | Fukunaga et al. |
| 5,585,007 A | 12/1996 | Antanavich et al. |
| 5,597,530 A | 1/1997 | Smith et al. |
| 5,605,255 A | 2/1997 | Reidel et al. |
| 5,605,541 A | 2/1997 | Holm |
| 5,638,661 A | 6/1997 | Banks |
| 5,643,206 A | 7/1997 | Fischer |
| 5,656,035 A | 8/1997 | Avoy |
| 5,665,067 A | 9/1997 | Linder et al. |
| 5,697,915 A | 12/1997 | Lynn |
| 5,728,075 A | 3/1998 | Levander |
| 5,735,465 A | 4/1998 | Laforcade |

(56) References Cited

U.S. PATENT DOCUMENTS

| | | |
|---|---|---|
| 5,752,626 A | 5/1998 | Bachand |
| 5,759,169 A | 6/1998 | Marx |
| 5,759,171 A | 6/1998 | Coelho et al. |
| 5,792,103 A | 8/1998 | Schwartz et al. |
| 5,810,885 A | 9/1998 | Zinger |
| 5,814,022 A | 9/1998 | Antanavich et al. |
| 5,814,066 A | 9/1998 | Spotnitz |
| 5,819,988 A | 10/1998 | Sawhney et al. |
| 5,824,012 A | 10/1998 | Burchett et al. |
| 5,830,547 A | 11/1998 | MacKenzie et al. |
| 5,842,326 A | 12/1998 | Wolf |
| 5,857,591 A | 1/1999 | Bachand |
| 5,871,700 A | 2/1999 | Konrad |
| 5,881,536 A | 3/1999 | Muller-Wille et al. |
| 5,888,408 A | 3/1999 | Nagels |
| 5,935,437 A | 8/1999 | Whitmore |
| 5,951,517 A | 9/1999 | Lampropoulos et al. |
| 5,964,377 A | 10/1999 | Demarest et al. |
| 5,968,018 A | 10/1999 | Freeman et al. |
| 5,976,102 A | 11/1999 | Epstein |
| 5,980,866 A | 11/1999 | Uchida et al. |
| 5,996,847 A | 12/1999 | Smolen, Jr. et al. |
| 5,997,811 A | 12/1999 | Esposito |
| 5,997,881 A | 12/1999 | Powell et al. |
| 6,001,259 A | 12/1999 | Whitmore |
| 6,010,034 A | 1/2000 | Walthers |
| 6,059,749 A | 5/2000 | Marx |
| 6,063,055 A | 5/2000 | Epstein et al. |
| 6,079,868 A | 6/2000 | Rydell |
| 6,099,511 A | 8/2000 | Devos et al. |
| 6,113,571 A | 9/2000 | Zinger et al. |
| 6,123,687 A | 9/2000 | Simonyi et al. |
| 6,132,396 A | 10/2000 | Antanavich et al. |
| 6,206,905 B1 | 3/2001 | Holm et al. |
| 6,234,994 B1 | 5/2001 | Zinger |
| 6,251,370 B1 | 6/2001 | Uchida et al. |
| 6,308,747 B1 | 10/2001 | Farris |
| 6,328,229 B1 | 12/2001 | Duronio et al. |
| 6,331,172 B1 | 12/2001 | Epstein et al. |
| 6,394,982 B1 | 5/2002 | Ehrenfels |
| 6,461,361 B1 | 10/2002 | Epstein |
| 6,471,670 B1 | 10/2002 | Enrenfels et al. |
| 6,475,193 B1 | 11/2002 | Park |
| 6,479,052 B1 | 11/2002 | Marshall et al. |
| 6,488,650 B1 | 12/2002 | Epstein et al. |
| 6,544,162 B1 | 4/2003 | Landin et al. |
| 6,648,133 B1 | 11/2003 | Blaschke et al. |
| 6,711,879 B2 | 3/2004 | Korteweg et al. |
| 6,830,762 B2 | 12/2004 | Baugh et al. |
| 6,959,812 B2 | 11/2005 | Reif et al. |
| 6,978,946 B2 | 12/2005 | Sweeton |
| 7,179,391 B2 | 2/2007 | Leach et al. |
| 7,223,346 B2 | 5/2007 | Dorian et al. |
| 7,374,678 B2 | 5/2008 | Leach et al. |
| 7,470,371 B2 | 12/2008 | Dorian et al. |
| 7,766,900 B2 | 8/2010 | Leach et al. |
| 8,137,329 B2 | 3/2012 | Romano et al. |
| 8,182,769 B2 | 5/2012 | Chavarria |
| 8,420,029 B2 | 4/2013 | Chavarria |
| 8,444,620 B2 | 5/2013 | Leach et al. |
| 8,518,272 B2 | 8/2013 | Hoeppner |
| 2001/0016709 A1 | 8/2001 | Tovey et al. |
| 2002/0035820 A1 | 3/2002 | Farris |
| 2002/0104808 A1 | 8/2002 | Blasetti et al. |
| 2002/0185457 A1 | 12/2002 | Smith et al. |
| 2003/0023203 A1 | 1/2003 | Lavi et al. |
| 2003/0029763 A1 | 2/2003 | Reif et al. |
| 2003/0139774 A1 | 7/2003 | Epstein et al. |
| 2003/0187408 A1 | 10/2003 | Marx |
| 2003/0189106 A1 | 10/2003 | Cernik |
| 2003/0201342 A1 | 10/2003 | Foster et al. |
| 2004/0024353 A1 | 2/2004 | Petersen et al. |
| 2004/0035743 A1 | 2/2004 | Tighe et al. |
| 2004/0065626 A1 | 4/2004 | Woo |
| 2004/0071786 A1 | 4/2004 | Grippi et al. |
| 2004/0108338 A1 | 6/2004 | Patel |
| 2004/0122383 A1 | 6/2004 | Romano et al. |
| 2004/0209755 A1 | 10/2004 | Moore et al. |
| 2004/0251217 A1 | 12/2004 | Leach et al. |
| 2005/0109716 A1 | 5/2005 | Leach et al. |
| 2005/0119424 A1 | 6/2005 | Ishii et al. |
| 2005/0196874 A1 | 9/2005 | Dorian et al. |
| 2005/0247715 A1 | 11/2005 | Ellsworth et al. |
| 2006/0009713 A1 | 1/2006 | Flaherty |
| 2006/0064070 A1 | 3/2006 | Martin |
| 2006/0175242 A1 | 8/2006 | Dorian et al. |
| 2006/0196885 A1 | 9/2006 | Leach et al. |
| 2006/0217674 A1 | 9/2006 | Romano et al. |
| 2006/0273049 A1 | 12/2006 | Leach et al. |
| 2006/0273050 A1 | 12/2006 | Higgins et al. |
| 2006/0278588 A1 | 12/2006 | Woodell-May |
| 2007/0012623 A1 | 1/2007 | Robinson et al. |
| 2008/0217264 A1 | 9/2008 | Leach et al. |
| 2008/0217265 A1 | 9/2008 | Leach et al. |
| 2008/0283474 A1 | 11/2008 | Leach et al. |
| 2009/0014391 A1 | 1/2009 | Leach et al. |
| 2009/0221075 A1 | 9/2009 | Dorian et al. |
| 2009/0250413 A1 | 10/2009 | Hoeppner |
| 2009/0253566 A1 | 10/2009 | Chavarria |
| 2010/0274206 A1 | 10/2010 | Leach et al. |
| 2012/0228291 A1 | 9/2012 | Chavarria |
| 2013/0255197 A1 | 10/2013 | Chavarria |
| 2013/0324913 A1 | 12/2013 | Leach et al. |
| 2013/0345038 A1 | 12/2013 | Hoeppner |

FOREIGN PATENT DOCUMENTS

| | | |
|---|---|---|
| DE | 632579 | 9/1936 |
| DE | 807113 | 6/1951 |
| DE | 3246999 A1 | 5/1984 |
| DE | 8913761 | 3/1990 |
| DE | 29516650 | 1/1996 |
| EP | 0208053 A2 | 1/1987 |
| EP | 0253418 A1 | 1/1988 |
| EP | 0253949 A2 | 1/1988 |
| EP | 0292472 | 11/1988 |
| EP | 0316284 A1 | 5/1989 |
| EP | 0432871 A2 | 6/1991 |
| EP | 0528949 A1 | 3/1993 |
| EP | 592242 | 4/1994 |
| EP | 0858776 | 8/1998 |
| FR | 840257 A | 4/1939 |
| FR | 2612782 | 9/1988 |
| FR | 2661097 | 10/1991 |
| FR | 2666986 A1 | 3/1992 |
| FR | 2668060 | 4/1992 |
| JP | 08238314 A | 9/1996 |
| JP | 08280802 A | 10/1996 |
| JP | 09108302 A | 4/1997 |
| WO | WO-8807874 | 10/1988 |
| WO | WO-9001959 | 3/1990 |
| WO | WO-9101711 | 2/1991 |
| WO | WO-9117778 A1 | 11/1991 |
| WO | WO-9419038 | 9/1994 |
| WO | WO-9639212 | 12/1996 |
| WO | WO-9725015 A1 | 7/1997 |
| WO | WO-9728834 | 8/1997 |
| WO | WO-9746203 A1 | 12/1997 |
| WO | WO-9747343 A1 | 12/1997 |
| WO | WO-9802098 A1 | 1/1998 |
| WO | WO-9810703 | 3/1998 |
| WO | WO-9810704 | 3/1998 |
| WO | WO-9813094 | 4/1998 |
| WO | WO-9840115 | 9/1998 |
| WO | WO-9901069 | 1/1999 |
| WO | WO-03018425 A1 | 3/2003 |

OTHER PUBLICATIONS

"The New Gold Standard" brochure for GPS® Mini and GPS® II Platelet Concentrate Separation Kit with ACD-A Anticoagulant, Biomet Biologics, Inc. (Dec. 2006), 7 pages.

(56) References Cited

OTHER PUBLICATIONS

Alving, B.M., M.J. Weinstein, et al. (1995). "Fibrin sealant: summary of a conference on characteristics and clinical uses." Transfusion 35(9): 783-90.
B. Braun/McGaw Product Catalog, May 1, 1999.
CFT Cell Factor Technologies, Inc., GPS® II Platelet Concentrate System, 2004 Biomet Orthopedics, Inc. (10 pages).
DePuy AcroMed, Inc., Symphony™ Platelet Concentrate System, 2001.
Developing Technologies for Accelerating Healing, Naturally®, Smart PReP® 2, Harvest® Technologies Corp. 2002 (6 pages).
Drug Intelligence and Clinical Pharmacy, vol. 22, pp. 946-952, Dec. 1988, Dennis F. Thompson, et al., "Fibrin Glue: A Review of Its Preparation, Efficacy, and Adverse Effects as a Topical Hemostat".
DynaStat™, Introducing DynaStat™ Surgical Hemostat—An Innovation in Hemostatic Biodevices, 2000 Cohesion Technologies, Inc.
FibriJet® 11:1 Ratio Applicator, Micromedics, Inc., printed from www.micromedics-usa.com/products/PDFs/FibriJet_Easy-Assembly.pdf, in 2005 (1 page).
FibriJet® product sheet, Micromedics, Inc., printed from www.micromedics-usa.com/products/PDFs/product_sheet.pdf, in 2005 (2 pages).
FibriJet® Ratio Applicator for application of platelet gel, Micromedics, Inc., printed from www.micromedics-usa.com/products/PDFs/ratio.pdf, in 2005 (1 page).
International Preliminary Examination Report issued Oct. 5, 2010 for PCT/US2009/039488 claiming benefit of U.S. Appl. No. 12/062,817, filed Apr. 4, 2008.
International Search Report mailed Jul. 10, 2009 for PCT/US2009/039488 claiming benefit of U.S. Appl. No. 12/062,817, filed Apirl 4, 2008.
Matras, H. (1985). "Fibrin seal: the state of the art." J Oral Maxillofac Surg 43(8): 605-11.
Matras, Helene, H. P. Dinges, H. Lassmann, and B. Mamoli. "Zur nahtlosen interfaszikularen Nerventransplantation im Tierexperiment." Wein Med Woschtr 122:37 (1972): 517-523.
OEM Products Catalog, Merit® Medical, available by Jan. 2003.
Prof. H. Stütz, M.D., et al., The Use of Autologous Fibrin Glue to Reduce Perioperative Blood Loss in Total Knee Arthroplasty—Results of a Controlled Study, Translated from the original article published in Orthopadische Praxis 40, 12 (2004).
Redl, H. and G. Schlag (1986). Fibrin Sealant and Its Modes of Application. Fibrin Sealant in Operative Medicine. G. Schlad and H. Redl. Heidelberg, Springer-Verlag: 13-26.
Redl, H.G. Schlag, et al. (1982). "Methods of Fibrin Seal Application." Thorac, cardiovasc. Surgeon 30: 223-227.
Shimada, J.K. Mikami, et al. (1995). "Closure of leaks by fibrin gluing. Effects of various application techniques and temperatures." J Cardiovac Surg (Torino) 35(2): 181-4.
Sierra, D. H. "Fibrin sealant adhesive systems: a review of their chemistry, material properties and clinical applications." *J Biomater Appl* 7 (Apr. 1993): 309-52.
Sporn, L.A., et al., (1995). "Cell proliferation on fibrin: modulation by fibrinopeptide cleavage." Blood 86(5): 1802-10.
Tange, R.A. (1986). "A New Application Method for Fibrin Sealant: The Glue Gun." Fibrin Sealant in Operative Medicine. G. Schlad and H. Redl. Heidelberg, Springer-Verlag.
Vox Sanq, vol. 68: 82-89, Feb. 1995, Boomgaard et. al, Pooled Platelet Concentrates Prepared by the Platelet-Rich-Plasma Method and Filtered with Three Different Filters and Stored for 8 Days.

STERILE BLOOD SEPARATING SYSTEM

CROSS-REFERENCE TO RELATED APPLICATIONS

This application is a divisional of U.S. patent application Ser. No. 12/062,801 filed on Apr. 4, 2008. The entire disclosure of the above application is incorporated herein by reference.

FIELD

The present disclosure relates to sterile devices, systems, and methods for separating components of a composition, such as blood.

BACKGROUND

The statements in this section merely provide background information related to the present disclosure and may not constitute prior art.

Whole blood includes a variety of different fractions or parts. For example, human whole blood includes platelet rich plasma (PRP), platelet poor plasma (PPP), red blood cells (RBCS), and white blood cells (WBCs). These different blood fractions have a variety of clinical and experimental uses. There is a need for devices and methods that separate and isolate the different fractions of whole blood. In particular, there is a need for devices and methods for separating and isolating different blood fractions in a non-sterile environment by non-sterile personnel for later use in a sterile environment.

SUMMARY

The present teachings provide for a system for separating components of a composition according to density. The system includes a torque generating device, a separation device, and a housing. The separation device separates the composition into different components according to density. The housing accommodates the separation device. The housing includes a base having an interface that transfers torque from the torque generating device to the separation device, a cover, and a conduit for introducing the composition into the separation device without opening the cover.

The present teachings further provide for a method for separating components of a composition according to density. The method includes: sealing a sterilized separation device within a container having a base and a cover such that the separation device is in cooperation with an interface at the base of the container; inserting the composition into the sterilized separation device sealed within the container by injecting the composition through a conduit that extends through the container and mates with the separation device; mating the container with a torque generating device, the interface in contact with both the torque generating device and the separation device; spinning the separation device using the torque generating device to separate the composition into different components according to density, the separation device is spun independent of the container and torque is transferred from the torque generating device to the separation device by the interface; removing the sterile separation device from the container; and withdrawing at least one of the different components from the separation device as necessary while the separation device is in the sterile environment.

The present teachings also provide for a container for housing a sterile separation device for separating components of a composition according to density. The container includes a container base, an interface, a cover, and a conduit. The container base has sidewalls extending from the container base to define a receptacle for accommodating the separation device. The interface is at the container base for transferring torque from a torque generating device to the separation device when the separation device is seated within the receptacle. The cover covers the receptacle and seals the sterile separation device within the receptacle to prevent contamination of the sterile separation device. The conduit extends through the container to the sterile separation device to permit delivery of blood through the container and into the sterile separation device when the sterile separation device is sealed within the receptacle.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses.

Figure 1:
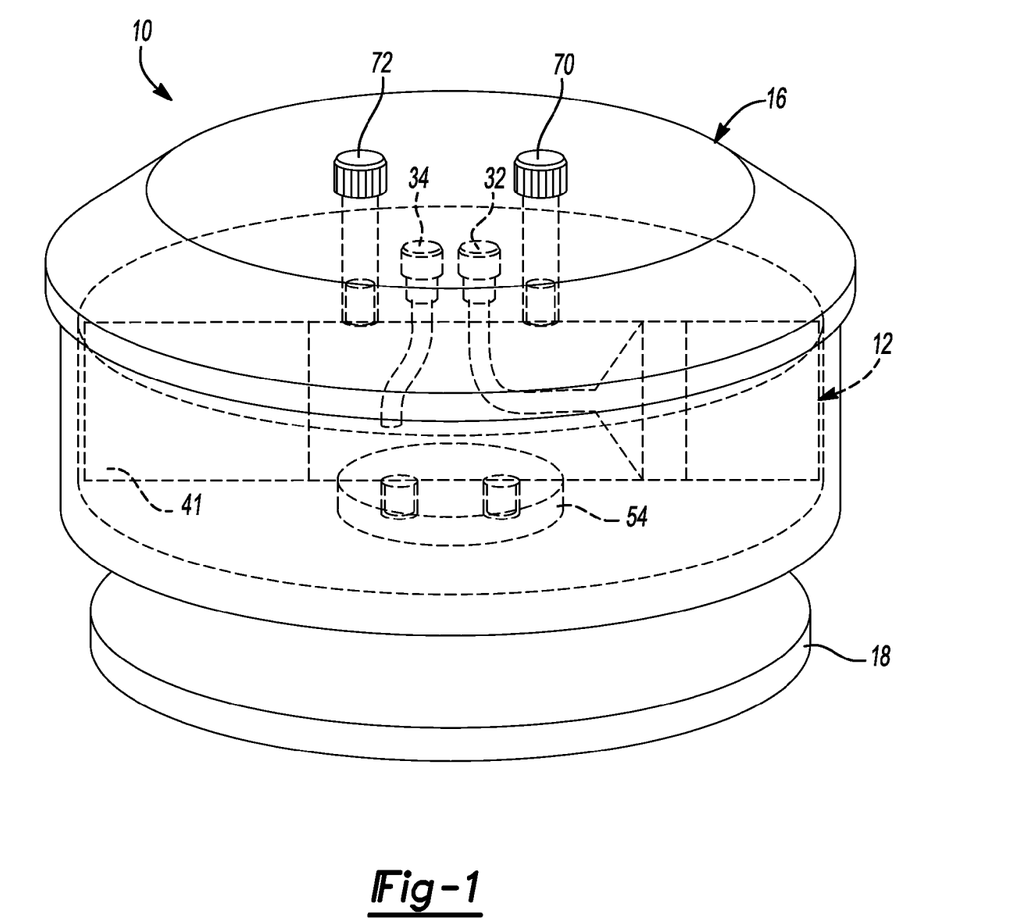
FIG. 1 is a perspective view of a system for separating components of blood according to the present teachings.
Figure 2:
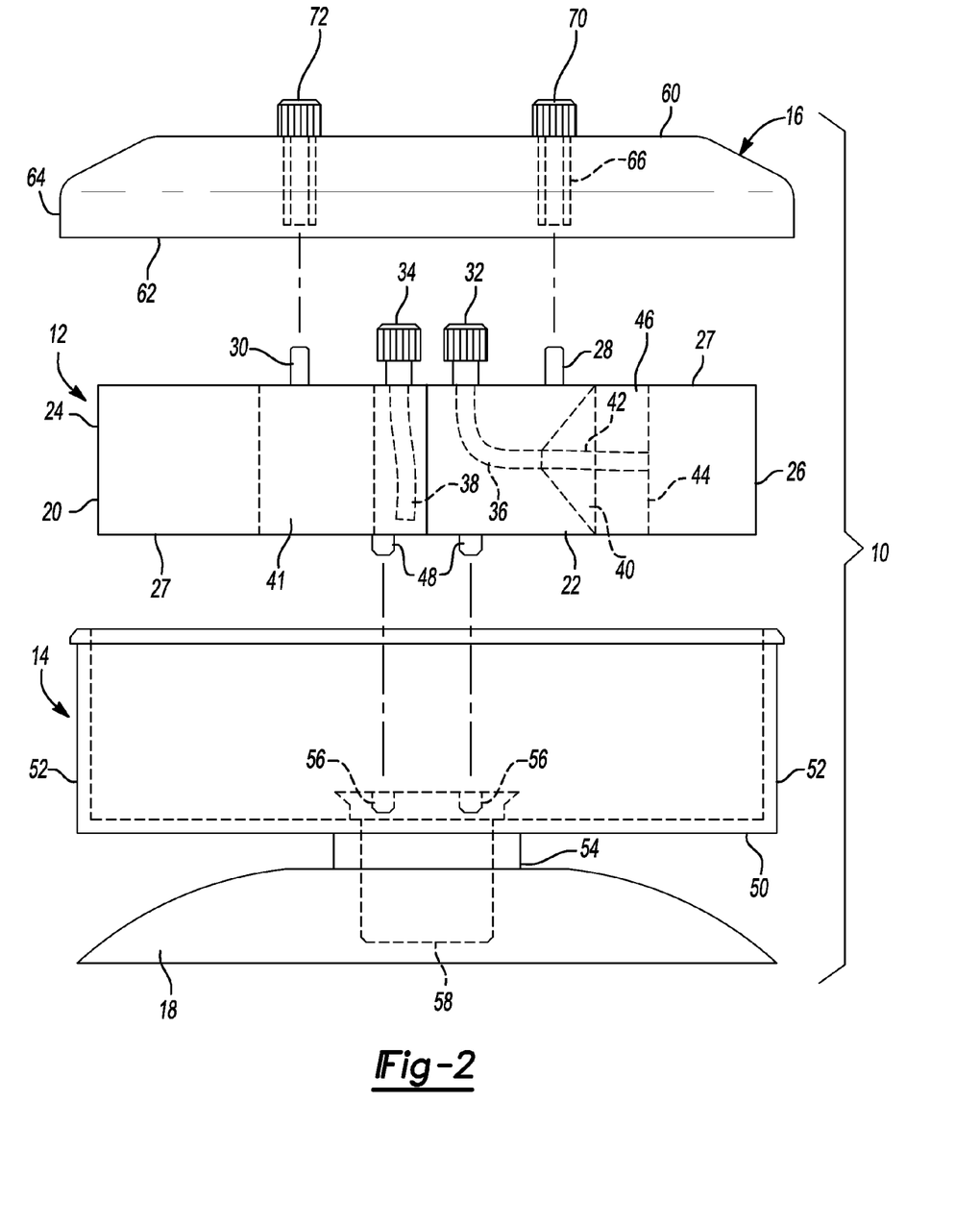
FIG. 2 is an exploded side view of the system of FIG. 1.
Figure 3:
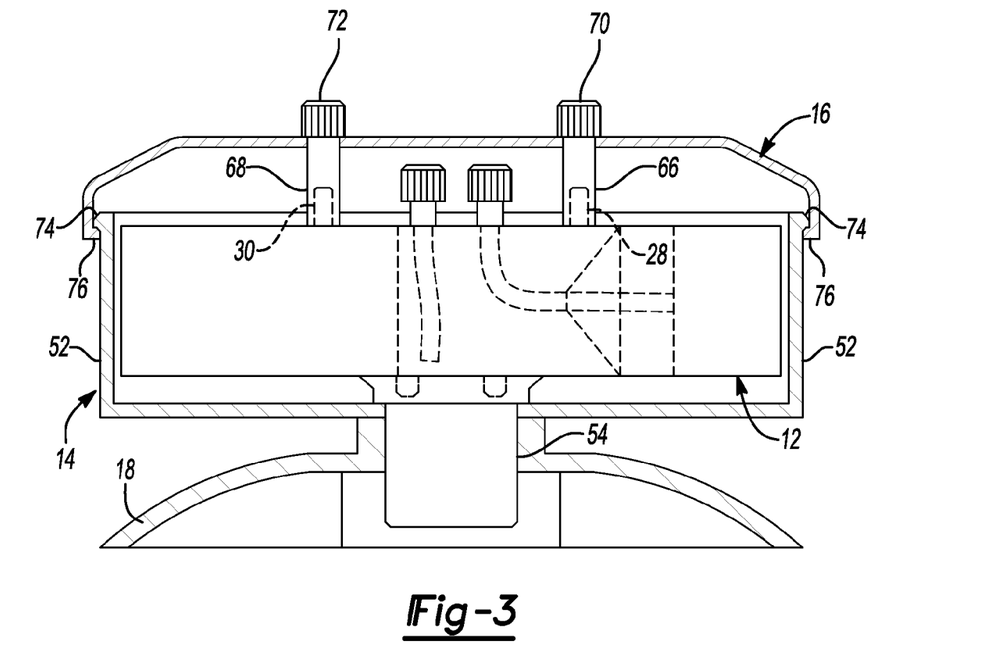
FIG. 3 is an assembled cross-sectional side view of the system of FIG. 1.

A system for separating components of a composition according to density is illustrated in FIGS. 1-3 at reference numeral 10. The system generally includes a component separation device 12, a container 14 for accommodating the separation device 12, a cover 16, and a motorized rotating platform 18. The system 10 can be used to separate components of a variety of compositions, such as whole blood as described herein.

The separation device 12 includes a main body 20 that defines a separation chamber 22. The main body 20 includes a first end 24, a second end 26, and a cylindrical sidewall 27 that extends between the first end 24 and the second end 26. The main body 20 is sized to fit within the container 14. While the separation device 12 described herein is merely an exemplary device, the device 12 is based off the separation devices of Biomet Inc.'s GPS system as described in, for example, U.S. Pat. No. 7,179,391 (filed May 23, 2003) and U.S. Publication Nos. 2005-0109716 (filed Sep. 2, 2004) and 2006-0273049 (filed May 25, 2006), which are hereby incorporated by reference. Differences between the device 12 and the separation tubes of the GPS devices include the location of the outlet ports 32 and 34 at the sidewall 27 and the presence of the locking details 48. In addition to the separation devices of the GPS, any suitable separation device can be used after being modified to include the locking details 48 and the outlet ports 32 and 34.

At the sidewall 27 is a first inlet port 28 and a second inlet port 30. The first and the second inlet ports 28 and 30 extend through the sidewall 27 to permit the introduction of materials into the separation chamber 22. As illustrated, the first and the second inlet ports 28 and 30 extend from the sidewall 27. However, the first and the second inlet ports 28 and 30 can be recesses in the sidewall 27 or can be co-planar with the sidewall 27, for example.

Also at the sidewall 27 is a first outlet port 32 and a second outlet port 34. The first and the second outlet ports 32 and 34 extend through the sidewall 27 to permit withdrawal of materials from within the separation chamber 22. As illustrated, the first and the second outlet ports 32/34 each extend from the sidewall 27 and are each covered with a removable cap. The first outlet port 32 includes a first outlet tube 36 and the second outlet port 34 includes a second outlet tube 38 that extends to within the separation chamber 22. The first outlet tube 36 and the second outlet tube 38 can each be directed to different areas of the separation chamber 22 to facilitate withdrawal of components at different regions of the separation chamber 22.

The separation device 12 can be configured to separate components of various different materials or substances by density. For example, the separation device 12 can be a blood component separation device to separate various components of whole blood by density, such as platelet rich plasma, red blood cells, platelets, and white blood cells. The separation device 12 is illustrated as an exemplary blood component separation device.

For example, as a blood component separation device the device 12 includes a separator (which includes a buoy 40 and a divider 44) and a counter-balance 41 at an end of the separation chamber 22 opposite to the buoy 40. The buoy 40 has a shape that conforms to the interior shape of the separation chamber 22. The buoy 40 has a tuned density that is configured to reach a selected equilibrium position in blood. For example, the buoy 40 can have a density tuned in the range from about 1.06 g/cc to about 1.11 g/cc, which is less than the density of red blood cells of whole blood. The buoy 40 has an access port 42 that extends through the buoy 40. The first outlet tube 36 of the first outlet port 32 is connected to the access port 42 of the buoy 40.

Mounted to the buoy 40 is the divider 44. The divider 44 is mounted to an end of the buoy 40 opposite to an end where the first outlet tube 36 enters the buoy 40. The divider 44 is mounted to the buoy 40 to create a collection compartment 46 between the divider 44 and the buoy 40. Components present within the collection compartment 46 can be withdrawn from within the separation chamber 22 through the access port 42, which extends to the collection compartment 46 and is in communication with both the first outlet tube 36 and the first outlet port 32.

The buoy 40 is movable within the separation chamber 22 laterally with respect to the first end 24 and the second end 26. When the separation device 12 is at rest, the buoy 40 forms an interference fit with the separation chamber 22 to hold the buoy at a position in the separation chamber 22. When the device 12 is rotated upon the platform 18, buoy 40 moves until it reaches an equilibrium within the composition being separated, such as whole blood. Material present in the separation chamber 22, such as blood, is able to pass between the buoy 40, as well as the divider 44, and the inner walls of the separation chamber 22. Alternatively, the buoy 40 and the divider 44 can have an opening to allow material to move through the buoy 40 and the divider 44.

The sidewall 27 of the main body 20 further includes one or more locking details 48 that are located opposite to the outlet ports 32 and 34. As illustrated, the locking details 48 protrude from sidewall 27. However, the locking details 48 can be of any shape, size, or configuration to provide cooperation with the container 14 and the rotating platform 18 to transfer torque from the platform 18 to the separation device 12.

The container 14 includes a container base 50 and cylindrical container sidewalls 52 that extend around the base 50. The base 50 and the sidewalls 52 define a receptacle sized to receive the separation device 12. The base 50 includes an interface 54. The interface 54 cooperates with the rotating platform 18 and receives the separation device 12 to transfer torque from the rotating platform 18 to the separation device 12. Between the interface 54 and the container 14 is a bushing to allow the interface 54 to rotate independent of the container 14. In particular, the interface 54 includes one or more receptacles 56 at a first end and a bottom portion 58 at a second end that is opposite to the receptacles 56. The receptacles 56 receive the locking details 48 of the separation device 12. The bottom portion 58 cooperates with the platform 18 to transfer torque from the platform 18 to the separation device 12.

The rotating platform 18 can be any suitable torque generating device. For example, the rotating platform 18 can be a Vortech type base by Biomet Biologics, Inc. of Warsaw, Ind.

The cover 16 includes an upper portion 60 and a lower portion 62. Side portions 64 extend between the upper portion 60 and the lower portion 62. A first conduit 66 and a second conduit 68 both extend through the cover 16. The first conduit 66 can include a first cap 70 and the second conduit 68 can include a second cap 72. As illustrated in FIG. 2, when the separation device 12 is seated in the container 14 and the cover 16 is on the container 14, the first conduit 66 is aligned with and connected to the first inlet port 28 and the second conduit 68 is aligned with and connected to the second inlet port 30. The connections between the conduits 66/72 and the ports 28/30 provide passages through the cover 16 to permit the introduction of blood, for example, through the cover 16 and into the separation device 12 when the cover 16 is in place over the device 12. The cover 16 can be independent of the container 14 or mounted to the container 14, such as with a hinge.

As illustrated in FIG. 3, the sidewalls 52 of the container 14 include locking details 74 at the ends of the sidewalls that are opposite to the container base 50. The locking details 74 of the container 14 cooperate with locking details 76 of the cover 16. Thus, the cover 16 is mounted to the container 14. To permit the separation device 12 to freely rotate within the container 14 when the cover 16 is in place, the conduits 66 and 68 are slidably removed to detach the cover 16 from the separation device 12, but not completely removed from the cover 16. In this regard, the passageway through the cover 16 that the conduits 66 and 68 are seated in remains filled so as to restrict the passage of bacteria and non-sterile materials through the cover 16. The cover 16 can also be mounted to the container 14 with a hinge at the sidewalls 52.

Figure 4:
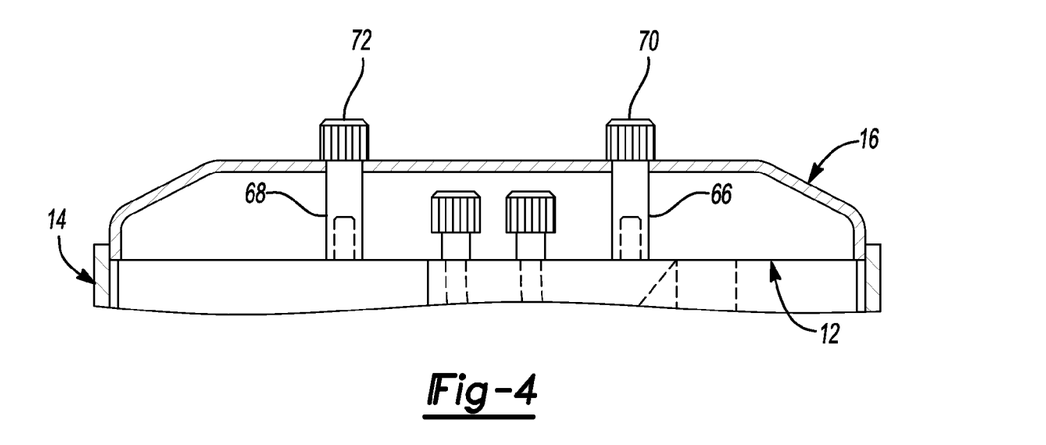
FIG. 4 is a cross-sectional side view of another system for separating blood components according to the present teachings.

With reference to FIG. 4, the system 10 can alternatively be provided with a cover 16 that is directly attached to the separation device 12. As a result, the cover 16 can rotate with the separation device 12 and the first and second conduits 66 and 68 do not need to be detached from the separation device 12 to permit rotation of the separation device 12. A bushing is provided between the cover 16 and the walls 52 of the container to reduce friction and allow the cover 16 to freely rotate within the container 14.

In use, the device 12, the container 14, and the cover 16 are sterilized. The sterile separation device 12 is placed in the sterile container and the sterile cover 16 is seated over the separation device 12 to prevent contamination of the separation device 12. With the separation device 12 sealed within the container 14, the container 14 can be handled by non-sterile personnel. For example, non-sterile personnel can transport the separation device 12 and/or load the separation device 12 with a composition to be separated, such as blood. For example, blood can be inserted into the separation device 12 through the first and/or second ports 28 and 30 using the first and/or second conduits 66 and 68.

After the separation device 12 is filled with blood, the container 14 is seated on the rotating platform 18. The separation device 12 is spun by the platform 18 for a suitable time at a suitable speed to generate a force of about 593×g. After the device 12 is spun as appropriate, the different components of blood will be separated according to density. For example, red blood cells typically settle between the divider 44 and the second end 26, a buffy coat of white blood cells and blood platelets typically settles in the collection compartment 46 between the buoy 40 and the divider 44, and platelet poor plasma typically settles between the counterbalance 41 and the buoy 40.

The sterile container 12 can then be opened and the separation device 12 can be removed by sterile personnel in the sterile environment or simply dumped into the sterile environment, such as onto a sterile tray. The desired blood fraction can be extracted through the first and/or the second outlet ports 32 and 34. For example, if blood platelets are desired to be extracted they can be extracted using the first outlet port 32 because the first outlet port 32, via the first outlet tube 36, extends to the collection compartment 46 where the platelets settle. Using the first outlet port 32, the red blood cells can be subsequently extracted after extraction of the platelets as the red blood cells can be withdrawn through and/or past the divider 44. If the platelet poor plasma is to be extracted, the second outlet port 34 can be used because the second outlet tube 38 extends to the region where the platelet poor plasma typically settles.

Thus, when sealed within the container 14, the sterile separation device 12 can be filled and spun by non-sterile personnel in a non-sterile environment. The container 14 can then be opened and the sterile separation device 12 can be removed and transferred to the sterile environment where the separated components can be withdrawn from the device 12 as necessary. Thus, while in the container 14 the sterility of the device 12 can be maintained even though the device is in a non-sterile environment, which offers greater flexibility for use and transport of the device 12.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A method for separating components of whole blood comprising:
    Sealing a sterilized separation device within a container having a base and a cover such that the separation device is in cooperation with an interface at the base of the container;
    Inserting whole blood into the sterilized separation device sealed within the container by injecting said whole blood through a conduit that extends through the container and mates with the separation device;
    Mating the container with a torque generating device, the interface in contact with both the torque generating device and the separation device;
    Spinning the separation device using the torque generating device to separate whole blood into different components according to density, the separation device is spun independent of the container and torque is transferred from the torque generating device to the separation device by the interface, wherein spinning the separation device causes a buoy to move within the separation device to separate different blood components, the buoy having a density less than that of red blood cells of the whole blood;
    Removing the sterile separation device from the container; and
    Withdrawing at least one of the different components from the separation device while the separation device is in a sterile environment.

2. The method of claim 1, further comprising inserting the composition into the sterilized separation device through a conduit that extends through the cover.

3. The method of claim 2, wherein inserting the composition into the sterilized separation device sealed within the container includes inserting the composition while the sterilized separation device is sealed within the container through the conduit.

4. The method of claim 1, further comprising spinning the separation device with a motorized rotating base.

5. The method of claim 1, further comprising sealing the separation device within the container by mounting the cover directly to sidewalls of the container.

6. The method of claim 1, further comprising sealing the separation device within the container by mounting the cover directly to the separation device.

7. A method for separating components of blood comprising:
    Positioning a sterilized separation device within a container having a base and a cover such that the separation device is in cooperation with an interface at the base of the container;
    Inserting the blood into the sterilized separation device sealed within the container by passing the composition through a conduit that extends through the container and mates with the separation device;
    Separating the blood into different components within the sterilized separation device that is within the container, wherein separating blood into different components includes settling red blood cells between a divider within the sterilized separation device and an end of the sterilized separation device, settling a buffy coat of white blood cells and blood platelets in a collection compartment between a buoy and the divider within the sterilized separation device, and settling platelet poor plasma between a counterbalance and the buoy; and
    Withdrawing at least one of the different components from the separation device while the separation device is in a sterile environment.

8. The method of claim 7, further comprising:
    seating the container on a base.

9. The method of claim 8, further comprising:
    operating the base to spin the sterilized separation device to separate the composition into different components within the sterilized separation device.

10. The method of claim 9, further comprising:
    removing the sterile separation device from the container after the composition is separated into different components.

11. The method of claim 9, wherein operating the base to spin the sterilized separation device includes spinning the sterilized separation device independent of the container.

12. The method of claim 11, further comprising:
sliding the conduit through the container in a first direction to engage a port of the sterilized separation device to allow inserting the composition into the sterilized separation device; and
sliding the conduit through the container in a second direction to disengage the port of the sterilized separation device to allow the sterilized separation device to spin independent of the container.

13. The method of claim 12, further comprising:
maintaining the conduit in a passage through the container while separating the composition into different components.

14. The method of claim 7, further comprising;
Removing the sterile separation device from the container after the blood is separated into different components;
Wherein withdrawing at least one of the different components from the separation device occurs after removing the sterile separation device from the container.

15. The method of claim 14, wherein the settled red blood cells, buffy coat, or platelet poor plasma is withdrawn as necessary.

* * * * *